United States Patent [19]

Ho

[11] Patent Number: 4,564,476
[45] Date of Patent: Jan. 14, 1986

[54] ARYL FATTY ACID LEUKOTRIENE SYNTHESIS INHIBITORS

[75] Inventor: Chih Y. Ho, Lansdale, Pa.

[73] Assignee: McNeilab, Inc., Fort Washington, Pa.

[21] Appl. No.: 665,683

[22] Filed: Oct. 29, 1984

[51] Int. Cl.[4] .................... C07C 57/42; C07C 69/108; C07C 103/76; C07C 33/30

[52] U.S. Cl. .................................. 260/404; 260/408; 260/410.9 N; 260/410.9 R; 260/413; 260/399; 568/59; 568/662; 568/812; 568/813; 568/765; 568/766; 514/549; 514/560; 514/627; 514/730

[58] Field of Search ................ 260/399, 408, 410.9 N, 260/410.9 M, 413 R, 413 Q, 404; 568/59, 662, 812, 813, 765, 766; 514/549, 560, 627, 730

[56] References Cited
PUBLICATIONS

"Synthesis and 5-Lipoxygenase Inhibitory Activity of 7,7-Dimethyleicosa-5Z,8Z-Dienoic Acid" by J. Ackroyd et al. which appeared in Tetrahedron Letters, vol. 24, No. 46, pp. 5139–5140 (1983).

*Primary Examiner*—Charles F. Warren
*Assistant Examiner*—Elizabeth A. Flaherty
*Attorney, Agent, or Firm*—David J. Levy

[57] ABSTRACT

Aryl fatty acid compounds of the formula (I)

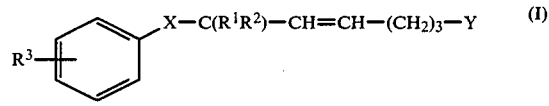

wherein $R^1$, $R^2$, $R^3$, X, and Y are as defined herein are novel and useful in the treatment of allergic and inflammatory disorders.

11 Claims, No Drawings

ARYL FATTY ACID LEUKOTRIENE SYNTHESIS INHIBITORS

BACKGROUND OF THE INVENTION

The metabolism of arachidonic acid via the lipoxygenase pathway gives rise to leukotrienes which are potent mediators of inflammation and allergic reactions. An object of the invention is a compound which would block the generation, release or action of leukotrienes to alleviate inflammation and allergic reactions.

SUMMARY OF THE INVENTION

Aryl fatty acid derivatives defined by the following formula (I):

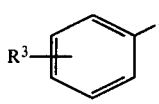

wherein $R^1$, $R^2$, $R^3$, X, and Y are defined herein are novel and useful in the treatment of certain inflammatory and allergic disorders in mammals, e.g. humans, such as asthma and other chronic obstructive pulmonary diseases, arthritis, psoriasis, chronic colitis, and myocardial infarction.

DETAILED DESCRIPTION OF THE INVENTION

The compounds of the present invention are of the following formula (I):

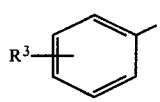

wherein
$R^1$ and $R^2$ are independently hydrogen, methyl or fluorine or taken together are ethylene of the formula —$CH_2CH_2$—;
$R^3$ is hydrogen, alkyl, alkoxy, alkylthio, halo, alkenyl or hydroxy;
X is —$CH_2OCH_2$—, —CH=CH—, or —CH=CH—$CH_2$—O—$CH_2$—;
Y is COOH, alkoxycarbonyl, —$CONH_2$, —$CONHR^4$, —$CONR^5R^6$, or hydroxyalkyl;
$R^4$ is alkyl or hydroxy;
$R^5$ is alkyl;
$R^6$ is alkyl; and,
when Y is —$CO_2H$, the pharmaceutically acceptable base addition salts thereof.

$R^3$, in more detail, is hydrogen; lower alkyl of about 1 to 6 carbons such as methyl, ethyl, propyl, isopropyl, n-butyl, sec-butyl, tert-butyl or hexyl; lower alkoxy of about 1 to 4 carbons such as methoxy, ethoxy, or tert-butoxy; loweralkylthio of about 1-4 carbons such as methylthio; and halo such as fluoro, chloro, bromo, or iodo; alkenyl of about two to six carbons such as ethenyl, propenyl, or hexenyl; or hydroxy. The $R^3$ group may be present at the 2-, 3- or 4-position of the phenyl ring.

X, in more detail, is —$CH_2OCH_2$—; ethenylene of the formula —CH=CH— wherein the hydrogens may be cis or trans; or —CH=CH—$CH_2$—O—$CH_2$— where the ethenylene portion is attached to the phenyl ring and the $CH_2$ group is attached to the carbon of formula (I) bearing the $R^1$ and $R^2$ groups.

Y, in more detail, is —$CO_2H$; loweralkoxycarbonyl wherein the loweralkoxy moiety is about 1 to 4 carbons such as methoxy, ethoxy, or tert-butoxy; —$CONH_2$; —$CONHR^4$; —$CONR^5R^6$; or hydroxyalkyl of about 1 to 4 carbons such as —$CH_2OH$.

$R^4$, in more detail, is loweralkyl of about 1 to 4 carbons such as methyl, ethyl, or tert-butyl; or hydroxy.

$R^5$ and $R^6$ are in particular, the same or different and are lower alkyl of about 1 to 4 carbons such as methyl, ethyl, or tert-butyl.

Specific compounds of the present invention are the following:
7,7-dimethyl-8-(phenylmethoxy)-5(Z)-octenoic acid;
N,N,7,7-tetramethyl-8-(phenylmethoxy)-5(Z)-octenamide;
ethyl 7,7-dimethyl-8-(phenylmethoxy)-5(Z)-octenoate;
7,7-dimethyl-8-(phenylmethoxy)-5(Z)-octen-1-ol;
7,7-dimethyl-8-(4-methoxyphenyl)methoxy-5(Z)-octenoic acid;
methyl 7,7-dimethyl-8-(4-methoxyphenyl)methoxy-5(Z)octenoate;
methyl 8-(4-hydroxyphenylmethoxy)-7,7-dimethyl-5(Z)octenoate;
8-(4-hydroxyphenylmethoxy)-7,7-dimethyl-5(Z)octenoic acid;
methyl 7,7-dimethyl-8-(phenylmethoxy)-5(Z)octenoate;
methyl 9-(4-chlorophenyl)-7,7-dimethyl-5(Z), 8-nonadienoate;
9-(4-chlorophenyl)-7,7-dimethyl-5(Z), 8-nonadienoic acid;
7,7-dimethyl-8-(3-phenyl-2-propenoxy)-5(Z)-octenoic acid; and
7,7-dimethyl-8-[[2-(1-pentenyl)phenyl]methoxy]-5(Z)octenoic acid.

When Y is —$CO_2H$, the compounds of formula I of this invention may form salts with a physiologically acceptable base such as sodium or potassium hydroxide, carbonate, or bicarbonate or an organic base such as tromethamine.

It is understood that the compounds of formula (I) may exist in various isomeric forms, e.g., cis/trans isomers formed in view of the presence of alkenyl groups as defined for $R^3$, X and in the backbone of the chain of formula (I), i.e., the —CH=CH— group of the —CH=CH—($CH_2$)$_3$— Y portion of formula (I), or optical isomers formed in view of the presence of an asymmetric carbon atom at the point of attachment of groups $R^1$ and $R^2$, when $R^1$ and $R^2$ are different.

The present invention includes all such individual cis/trans and optical isomers. In addition, compounds of formula (I) may exist in hydrated or solvated forms and the invention includes all such forms. As used in the present specification, the terms "alkyl", "alkoxy", "loweralkyl", and "loweralkoxy" include all straight and branched chain alkyl or alkoxy groups within the carbon limits defined.

The double bond in the 5-position shown in the —CH=CH—($CH_2$)$_3$—Y portion of formula (I) may exist in the cis (Z) or trans (E) configuration. The preferred configuration is cis.

Compounds of the formula (I) as defined above may be prepared by the following synthetic routes (A) and (B).

(A) Diol Route

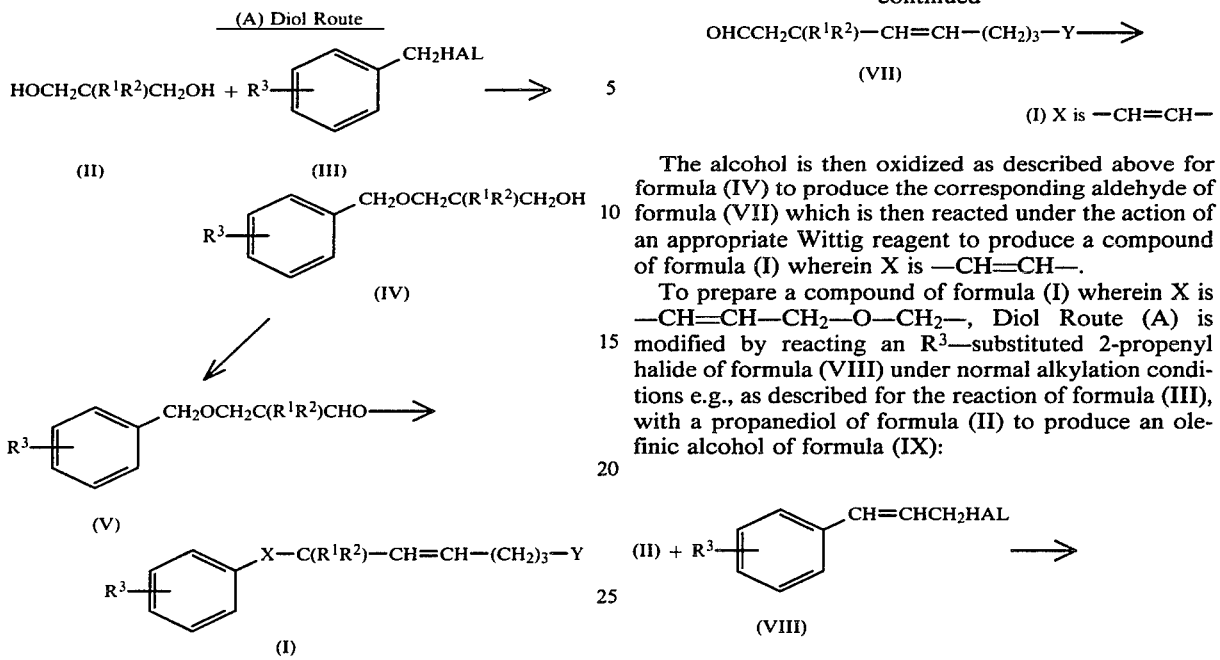

In the Diol Route (A), a propanediol of formula (II) is alkylated with a benzyl halide of formula (III) to produce a monosubstituted benzyloxy propanol of formula (IV). The propanol (IV) is oxidized to form an aldehyde of formula (V) which is then reacted under Wittig conditions to form the alkenes of formula (I) where X is —CH$_2$—O—CH$_2$—. Such products of formula (I) may be further carried on to those wherein X is —CH=CH—. The route may be modified by replacement of formula (III) to yield formula (I) products wherein X is —CH=CH—CH$_2$—O—CH$_2$—.

In more detail, a substituted propanediol of formula (II) is reacted with an alkali metal hydride such as sodium hydride or potassium hydride in a polar aprotic solvent, e.g., dimethyl formamide (DMF) or tetrahydrofuran (THF). Alkylation of the thus formed anion is accomplished by reaction with an appropriately substituted benzyl halide of formula (III) under normal alkylation conditions, e.g., at about 0° to 100° C., to form a substituted benzyloxypropanol of formula (IV). The propanol is then oxidized under standard oxidation conditions by the action of pyridinium dichromate e.g., at 0° to 50° C., in a solvent such as methylene chloride to produce an aldehyde of formula (V). The aldehyde is then reacted under normal Wittig conditions with an appropraite Wittig reagent to yield the final product alkenes of formula (I), wherein X is —CH$_2$OCH$_2$—.

To prepare compounds of formula (I) wherein X is —CH=CH—, a compound of formula (I) where X is —CH$_2$OCH$_2$— is first debenzylated under the action of sodium in liquid ammonia at about −78° to 25° C. to produce an alcohol of formula (VI):

(I) X = —CH$_2$OCH$_2$— ⟶

HOCH$_2$C(R$^1$R$^2$)—CH=CH—(CH$_2$)$_3$—Y ⟶

(VI)

-continued

OHCCH$_2$C(R$^1$R$^2$)—CH=CH—(CH$_2$)$_3$—Y ⟶

(VII)

(I) X is —CH=CH—

The alcohol is then oxidized as described above for formula (IV) to produce the corresponding aldehyde of formula (VII) which is then reacted under the action of an appropriate Wittig reagent to produce a compound of formula (I) wherein X is —CH=CH—.

To prepare a compound of formula (I) wherein X is —CH=CH—CH$_2$—O—CH$_2$—, Diol Route (A) is modified by reacting an R$^3$—substituted 2-propenyl halide of formula (VIII) under normal alkylation conditions e.g., as described for the reaction of formula (III), with a propanediol of formula (II) to produce an olefinic alcohol of formula (IX):

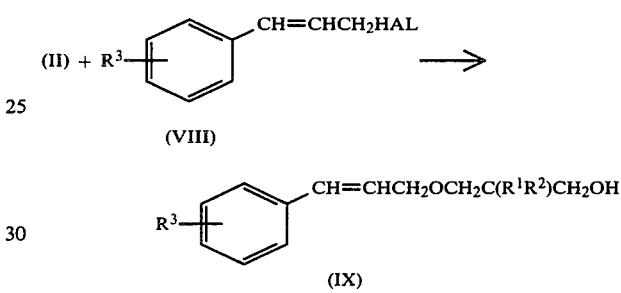

Alcohol (IX) is then oxidized to the corresponding aldehyde and reacted under Wittig conditions, as described above for formula (V) to produce the final product. Compounds of formula (I) wherein Y represents an amide function of formula —CONH$_2$, —CONHR$^4$ or —CONR$^5$R$^6$ are prepared by standard techniques such as conversion of the corresponding acid of formula (I) where Y is —COOH to an acyl halide, by the action of thionyl chloride or PBr$_3$ and the like reagents, at about 0° to 100° C. followed by reaction of the acyl halide with ammonia or an appropriate amine of formula R$^4$NH$_2$ or R$^5$R$^6$NH, respectively, e.g., at about 0° to 50° C. To prepare compounds of formula (I) wherein R$^4$ is hydroxy, hydroxylamine may be used in place of an amine.

Compounds of formula (I) wherein Y represents an ester function may be prepared from the corresponding acids of formula (I) by standard esterification procedures, such as by the action of an alcohol in the presence of a strong mineral acid e.g., ethanol in the presence of sulfuric acid. Alternatively, an acid of formula (I) may be converted to a methyl ester by the action of diazamethane under standard conditions.

Conversely, an ester of formula (I) where Y is alkoxycarbonyl may be converted by mild hydrolysis techniques to the corresponding acid. For example, an ester of formula (I) is hydrolyzed in methanol solution to its corresponding acid by the action of aqueous potassium carbonate over a period of one to two days at room temperature.

Compounds of formula (I) wherein Y represents —CH$_2$OH are prepared from the corresponding esters by standard hydride reduction techniques. For example, an ester of formula (I) where Y is alkoxycarbonyl is reacted with lithium aluminum hydride in an aprotic ethereal solvent, such a diethyl ether or THF to produce a compound of formula (I) wherein Y is —CH$_2$OH.

To prepare the compound of formula (I) wherein R$^1$ and R$^2$ taken together are ethylene of the formula —CH$_2$CH$_2$—, the method of K. C. Nicolaou described in Volume 48 of The Journal of Organic Chemistry, pp. 5401 (1983) is employed to first produce 2,2-ethanoformylacetic acid, which is then esterified by the action of diazomethane and subsequently converted to an alkene by standard Wittig conditions using (4-carboxybutyl)-triphenylphosphine bromide in DMSO to produce 6-(1-methoxycarbony 1-cyclopropyl)-5(Z)-hexenoic acid. The ester is then reduced by the action of LAH in ether to produce an alcohol of formula (VI) which is then treated as shown above to produce the target compound.

(B) Aldehyde Route

An alternate route to prepare compounds of formula (I) wherein X is —CH$_2$OCH$_2$— is by the aldehyde route, shown below.

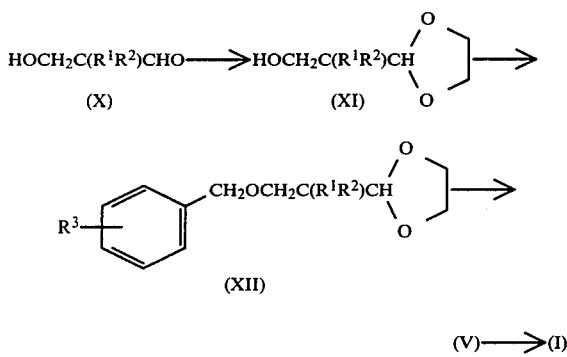

In this procedure, a hydroxyalkylaldehyde of formula (X) is first protected by conversion to its corresponding acetal of formula (XI) and then alkylated with an appropriately substituted benzyl halide to produce a benzyloxy acetal of formula (XII). The acetal is then converted to the aldehyde of formula (V) and reacted to produce final products as described for Route (A).

In more detail, a β-hydroxypropionaldehyde of formula (X), prepared by the method of E. T. Stiler, et al., which is described in the Journal of the American Chemical Society 1785 (1940), is reacted with ethylene glycol in refluxing toluene in the presence of a catalytic amount of p-toluenesulfonic acid under Dean Stark conditions to produce a β-hydroxy acetal of formula (XI). The acetal is then alkylated with a benzyl halide of formula (III) as described above under normal alkylation conditions, e.g. with sodium hydride in DMF solution to produce a benzyloxy acetal of formula (XII). The benzyloxy acetal is then hydrolyzed under normal deprotection conditions, e.g., heating in aqueous hydrochloric acid and THF solution at about 40° to 80° C. for about 10 to 24 hours to produce the aldehyde of formula (V). The aldehyde is then reacted as described above in Route (A) to produce the corresponding compound of formula (I).

The compounds of formula (I) of this invention have been demonstrated to possess valuable antialleric and antiinflammatory properties by virtue of the following in vitro tests.

(a) Immunologically Mediated Contraction of the Parenchymal Strip (IMCPS)

This test demonstrates the effectiveness of an agent in preventing the contraction of guinea pig lung parenchymal tissue by blocking immunological release of leukotriene products of the lipoxygenase pathway. It is a modification of the procedure published by K. Forsberg and L. Sorenby in Agents and Actions, Vol. 9 pp. 364–368 (1978). In this test, male Hartley strain guinea pigs weighing 400 to 600 g were sensitized by subcutaneous administration of chicken egg albumin (Sigma A-5503, 1.0 mg, 0.5% solution) and bordetella pertussis, $11 \times 10^9$ cells (Massachusetts Public Health Biological Labs) 4 to 8 weeks prior to the experiment. The animals were sacrificed, the heart and lungs were removed en bloc and placed in Krebs solution at room temperature. Lung strips (2.5 cm in length) were cut from the peripheral edge of each lobe. Two strips were removed from each animal and were trimmed to be of equal length. Each strip was suspended in an isolated organ bath (10.0 ml) containing oxygenated Krebs buffer solution at 37.5° C. then attached to a force displacement transducer (Grass FT03) and placed under an initial tension of 1.0 g. The tissues were allowed to equilibrate for 45–60 minutes, during which the bathing solution was changed several times. At the end of the equilibration period, chlorpheniramine (10.0 μM) and indomethacin (100.0 μM) were added to eliminate the contribution of histamine and prostaglandins to the contractile response. The two tissues from each animal were matched so that one tissue served as a control, and the test drug dissolved in DMSO was added to the bath containing the other tissue at a final concentration of 100 μM. After 30 minutes, egg albumin was added to each bath and the contractile response was measured as milligrams of tension developed as recorded on a Grass Model 7D polygraph. A test compound is considered active if it demonstrates a 15% or greater inhibition in contraction of a guinea pig parenchymal strip, relative to the control tissue, at a drug concentration of 100 μM.

(b) Human Granulocyte Assay for Lipoxygenase Products (HGALP)

This test is a measurement of the inhibition of the synthesis or release of [3H]-labeled lipoxygenase metabolites released or generated from human granulocyte cells that are prelabeled with [3H]-arachidonic acid. These metabolites include the leukotrienes (e.g., LTB$_4$) which are potent mediators of inflammation and allergy. In this test, a granulocyte enriched fraction is prepared from freshly drawn human blood (50 ml/donor) by standard techniques involving unit gravity separation on ficoll hypaque. Cells are prelabeled with [3H]-arachidonic acid (20 μCi in 2 ml cell suspension) during a 30 min. incubation at 37° C. After washing out unincorporated label, the radiolabeled cells are brought up in incubation buffer (Minimum Essential Medium containing 14 μM indomethacin) to a 10$^7$ cell/ml concentration. Cell suspensions (1 ml/sample) are preincubated for 5 min. in the presence or absence of test drugs delivered in 5 μl dimethylsulfoxide (DMSO). Cell suspensions are challenged with 10 μM ionophore A23187 to activate the calcium-dependent metabolism of [3H]-arachidonic acid. After a 5 min. incubation at 37° C., incubations are terminated by the addition of 1 ml ice cold phosphate buffered saline, and cells are pelleted by centrifugation. Supernatants are passed through C18

Sep Pak ® cartridges which are then washed twice with 1 ml water. Lipoxygenase metabolites are eluted with two 1 ml volumes of methanol. Eluates are collected in scintillation vials and counted in Aqueous Counting Scintillant (ACS). Radioactivity eluted with methanol is a measure of lipoxygenase metabolites. Values are normalized to vehicle (5 µl DMSO) treated controls and expressed as percent inhibition. Triplicate determinations at each drug concentration are analyzed as log-dose response curves by linear regression analysis from which $IC_{50}$ values are derived. The compounds of formula (I) of this invention are considered active in the HGALP test if they exhibit an inhibition or provide an estimate of potency in an $IC_{50}$ (concentration which produces a 50% inhibition).

The results of the IMCPS and the HGALP tests, employing the administration of various illustrative compounds of the present invention, are shown in Table I wherein $R^1$ and $R^2$ are both methyl.

TABLE I

Effect of test compounds in the IMCPS and HGALP tests.

$$R^3 \text{—} \bigcirc \text{—} X\text{—}C(R^1R^2)\text{—}CH\text{=}CH\text{—}(CH_2)_3\text{—}Y \quad (I)$$

| Example | $R^3$ | X | Y | IMCPS % inhib. 100 µM | HGALP $IC_{50}$ (µM) |
|---------|-------|---|---|------|-----|
| 1c | H | —CH$_2$OCH$_2$— | —CO$_2$H | 79 | |
| 2 | " | " | —CON(CH$_3$)$_2$ | 19 | 42 |
| 4 | " | " | —CH$_2$OH | 38 | 17 |
| 5c | 4-OCH$_3$ | " | —CO$_2$H | 31 | 18% @ 100 µM |
| 6 | 4-OH | " | —CO$_2$CH$_3$ | 49 | 39 |
| 7 | " | " | CO$_2$H | 4 | 255 |
| 8c | 4-Cl | —CH=CH— | —CO$_2$CH$_3$ | 15 | 6.6 |
| 9 | " | " | —CO$_2$H | 76 | 19 |
| 10c | H | —CH=CH—CH$_2$OCH$_2$— | —CO$_2$H | 44 | 5% @ 100 µM |
| 11g | 2-(1-pentenyl) | —CH$_2$OCH$_2$— | " | 40 | 96 |

Also part of the present invention are pharmaceutical compositions and methods, e.g., for the treatment of allergic reactions and inflammatory disorders using such compositions. To prepart the pharmaceutical compositions of this invention, one or more compounds or salts thereof of the invention as the active ingredient, is intimately admixed with a pharmaceutical carrier according to conventional pharmaceutical compounding techniques. One particular route of administration would employ administration of the active compound of formula (I) by means of an inhalation device. An example is a turboinhaler such as the Spinhaler ® device produced by Fisons Corp. of Bedford, Mass. for Intal ® brand of cromolyn sodium. In this system, a compound of formula (I) may be micronized together with a lactose carrier and inhaled with the use of the Spinhaler. Alternatively, the active compound may be made into a nebulizer water solution or suspension and used as mist after being nebulized with an appropriate air nebulizer in a manner similar to that used with Intal ® brand of cromolyn sodium. Another inhaler device which can be used for the compounds of formula (I) is the Beclovent ® inhaler obtained from Glaxo, Inc. of Research Triangle Park, NC. In this system, a suspension of the active ingredient in propellants such as trichloromonofluoromethane or dichlorodifluoromethane and oleic acid is provided and each activation of the inhaler cannister delivers a metered dose to be inhaled by the patient having allergic symptoms.

The pharmaceutical inhalation compositions herein will contain per dosage unit from about 0.01 to about 10.0 mg of the active ingredient, and, preferably, from about 0.01 to about 1.0 mg.

Alternate routes of administration of the compounds of formula (I) of this invention may be by injection, either subcutaneously or intraveneously. When administered by the subcutaneous route, the dosage unit will contain from about 1 to 100 mg of the active ingredient, and, preferably from about 0.1 to 1.0 mg. When administered by the intraveneous route, the dosage unit will contain from about 0.1 to 20 mg of the active ingredient, and preferably from about 0.1 to 1.0 mg.

In the following examples and throughout the specification, the following abbreviations may be used: mg (milligrams); g (grams); kg (kilograms); ml (milliliters); mmole (millimoles); µM (micromolar); mM (millimolar); M (molar); N (normal); psi (pounds per square inch); mp (melting point); bp (boiling point); meq (milliequivalents); E (trans); Z (cis); Et$_2$O (diethyl ether); EtOAc (ethyl acetate); MeOH (methanol); EtOH (ethanol); i-PrOH (iso-propanol); LAH (lithium aluminum hydride); THF (tetrahydrofuran); DMF (dimethylformamide); s.c. (subcutaneous); i.v. (intravenous); and C,H,N,O, etc. (the chemical symbols for the elements). Unless otherwise indicated, all temperatures are reported in ° C. (degrees centigrade).

The following examples are intended to describe the preparation of various compounds of formula (I) of this invention. They are to be considered representative of the chemistry employed, but not to be considered limiting as to scope or to kind.

EXAMPLE 1 a. 2,2-Dimethyl-3-(phenylmethoxy)-propanol

A mixture of 29.0 g (1.2 moles) of sodium hydride and 200 ml of dry DMF was stirred under an atmosphere of N$_2$ and cooled with an ice-water bath. A solution of 125 g (1.20 moles) of 2,2-dimethylpropandiol in 100 ml of dry DMF was added with stirring. After the hydrogen gas evolution ceased, 139 ml (1.20 moles) of benzyl chloride was added and the reaction mixture was stirred at room temperature overnight. The resulting reaction solution was poured into ice-water (300 ml) and the aqueous solution was extracted with ethyl ether three times. The organic solutions were combined and washed with NaCl solution and then dried over $Na_2SO_4$. The residue, after removal of solvent, was distilled through a vigreux column to obtain the title compound, bp. 85°–87°/0.02 mmHg, as a colorless liquid.

b. 2,2-Dimethyl-3-(phenylmethoxy)-propionaldehyde

In a dry three-neck flask equipped with a mechanical stirrer and an addition funnel was placed 78.8 g (0.21 moles) of pyridinium dichromate, Aldrich Chemical, see Tetrahedron Lett., 399 (1979), ibid., 731, (1980) and 200 ml of dry $CH_2Cl_2$. The mixture was vigorously stirred and a solution of 26.8 g (0.138 mole) of 2,2-dimethyl-3-(phenylmethoxy)propanol, the product of Example 1a, in 50 ml of $CH_2Cl_2$ was added in one portion. The reaction was followed by gas liquid chromatography (GC) and required four days stirring at room temperature. The black brown reaction mixture was poured into 200 ml ethyl ether and the mixture was filtered through a dry silica gel column to obtain a colorless solution. Removal of solvent gave a residue which was distilled through a vigreux column to obtain the title compound, a colorless liquid, bp 72°–75°/0.02 mmHg.

c. 7,7-Dimethyl-8-(phenylmethoxy)-5(Z)-octenoic Acid

Formula (I): $R^1=CH_3$; $R^2=CH_3$; $R^3=H$; $X=-CH_2OCH_2-$; $Y=-CO_2H$.

Into a dry three-neck flask equipped with an addition funnel, a gas bubbler, magnetic stirrer, and under an atmosphere of $N_2$ was placed 3.90 g. (0.163 mole) of sodium hydride and 81 ml of dry DMSO (freshly distilled over $CaH_2$). The flask was heated (82° C.) in an oil bath until the gas evolution ceased. The obtained greenish solution was cooled to room temperature and a solution of 35.7 g (0.0805 mole) of (4-carboxybutyl) triphenylphosphonium bromide, from Aldrich [see J. Am. Chem. Soc., 92 397 (1970)], ibid., 95, 6831, 7185 (1973) and 120 ml of DMSO was added dropwise. After the addition, a solution of 12.9 g (0.067 mole) of 2,2-dimethyl-3-(phenylmethoxy) propionaldehyde, the product of Example 1b, in 10 ml DMSO was added and stirring at room temperature was continued overnight. The reaction mixture was poured into ice-water mixture and acidified with 3N HCl. The aqueous solution was extracted with three 300 ml portions of ethyl ether. The combined ether solution was washed with 2.8N $NH_4OH$ solution in small portions until the obtained aqueous solution was basic. The washed aqueous solutions were combined and acidified with 3N HCl. The acidified solution was extracted with three 100 ml portions of ethyl ether. The obtained organic solution was washed once with sodium chloride solution and dried over magnesium sulfate. Removal of solvent on a rotary evaporator under reduced pressure gave an oily residue. The residue was distilled through a Kugelrohr distillation apparatus to give the title compound, b.p 151°–161°/0.02 mm Hg.

Elemental Analysis:
Calculated for $C_{17}H_{24}O_3$: C, 73.88; H, 8.75.
Found: C, 73.21; H, 8.59.

EXAMPLE 2

N,N,7,7-Tetramethyl-8-(phenylmethoxy)-5(Z)-octenamide

Formula (I): $R^1=CH_3$; $R^2=CH_3$; $R^3=H$; $X=-CH_2-O-CH_2-$; $Y=CONR^5R^6$; $R^5=CH_3$; $R^6=CH_3$.

A mixture of 5.64 g (0.02 mole) of 7,7-dimethyl-8-(phenylmethoxy)-5(Z)-octenoic acid, the product of Example 1c, 100 ml of dry toluene and 7 ml of thionylchloride was heated to reflux for 1.5 hours. Excess thionyl chloride was removed under reduced pressure. The resulting crude acid chloride was dissolved in toluene and treated with excess dimethylamine in toluene at 0° C. The reaction mixture was poured into an ice-water mixture and extracted with one 150 ml portion of ethyl acetate. The organic solution was washed with brine and dried over magnesium sulfate. Removal of solvent in vacuo gave a residue which was chromatographed on a silica gel column with $CHCl_3$ as an eluent. The obtained product was distilled through a Kugelrohr apparatus to give the title compound, bp 150°–160°/0.025 mmHg.

Elemental Analysis:
Calculated for $C_{19}H_{29}NO_2$: C, 75.21; H, 9.63; N, 4.62.
Found: C, 75.02; H, 9.65; N, 4.61.

EXAMPLE 3

Ethyl 7,7-dimethyl-8-(phenylmethoxy)-5(Z)-octenoate

Formula (I): $R^1=CH_3$; $R^2=CH_3$; $R^3=H$; $X=-CH_2OCH_2-$; $Y=-COOCH_2CH_3$.

A solution of 4.30 g of 7,7-dimethyl-8-(phenylmethoxy)5(Z)-octenoic acid the product of Example 1c, in 50 ml of ethyl alcohol containing two drops of conc. $H_2SO_4$ was refluxed for 12 hours. The reaction solution was cooled to room temperature and 5 g of $NaHCO_3$ was added to neutralize the acid. Solvent was removed to obtain a residue. The residue was dissolved in ethyl ether and then successively washed with sodium bicarbonate solution and sodium chloride solution. Drying and removal of the solvent yielded ethyl 7,7-dimethyl-8-(phenylmethoxy)-5-(Z)-octenoate.

EXAMPLE 4

7,7-Dimethyl-8-(phenylmethoxy)-5(Z)-octenol

Formula (I): $R^1=CH_3$; $R^2=CH_3$; $R^3=H$; $X=-CH_2OCH_2-$; $Y=-CH_2OH$.

A mixture of 0.70 g of lithium aluminum hydride in 50 ml of diethyl ether was cooled in an ice-water bath. A solution of 4.22 g of the ethyl ester obtained in Example 3 was added dropwise with stirring over a 1 hour period. The reaction was quenched by successive addition of 0.7 ml $H_2O$, 0.7 ml of 15% NaOH, and 2.1 ml of $H_2O$. Stirring was continued for an additional 1 hour and the white solid was filtered off. The obtained filtrate after removal of the solvent gave the crude product, which was distilled through a Kugelrohr apparatus to obtain the title compound, bp 120°/0.025 mm Hg.

Elemental Analysis:
Calculated for $C_{17}H_{26}O_2$: C, 77.82; H, 9.99.
Found: C, 77.90; H, 9.81.

EXAMPLE 5 a. 2,2-Dimethyl-3-(4-methoxyphenylmethoxy)-propanol

A mixture of 7.7 g (0.32 mole) of sodium hydride and 80 ml of DMF was stirred under an atmosphere of $N_2$ and cooled with an ice-water bath. A solution of 33 g (0.32 mole) of 2,2-dimethylpropandiol in 100 ml of DMF was added dropwise. Stirring was continued until the gas evolution stopped, then a solution of 50 g (0.32 mole) 4-methoxybenzyl chloride was added. The reaction mixture was stirred at room temperature overnight. The resulting solution was poured into an ice-water mixture and the aqueous solution was extracted with ethyl ether three times. The ether solution was washed with H$_2$O, saturated brine, and then dried over MgSO$_4$. The residue, after removal of solvent, was distilled through a vigreux column to obtain the title compound, bp 115°-120°/0.02 mm Hg, a colorless liquid.

b.
2,2-Dimethyl-3-(4-methoxyphenylmethoxy)propionaldehyde

In a dry three-neck flask equipped with a mechanical stirrer and an addition funnel was placed 110 g of pyridinium dichromate and 200 ml of dry CH$_2$Cl$_2$. The mixture was stirred vigorously and then 42 g of 2,2-dimethyl-3-(4-methoxyphenylmethoxy)propanol, the product of Example 5a, was added in one portion. The resulting reaction mixture was stirred for 4 hours. The black brown mixture was poured into 400 ml ethyl ether and the mixture was filtered through a dry silica gel column to obtain a colorless solution. Removal of the solvent gave a residue which was distilled through a vigreux column to obtain the title compound, bp 83°-100°/0.25 mm Hg.

c.
7,7-Dimethyl-8-(4-methoxyphenylmethoxy)-5(Z)-octenoic Acid and the Methyl Ester Formula (I): R$^1$=CH$_3$; R$^2$=CH$_3$; R$^3$=4-OCH$_3$; X=—CH$_2$OCH$_2$—; Y=—COOH and Y=—COOCH$_3$.

Into a dry three-neck flask under an atmosphere of N$_2$ was placed 4.99 g (0.21 mole) of NaH and 100 ml of DMSO. The flask was heated in an 80° C. oil bath until the gas evolution stopped. The reaction mixture was allowed to cool to room temperature, then a solution of 46.0 g gram (0.104 mole) of (4-carboxybutyl)triphenylphosphonium bromide in 30 ml DMSO was added dropwise, followed by addition of a solution of 21.9 g (0.099 mole) of 2,2-dimethyl-3-(4-methoxyphenylmethoxy)propionaldehyde, the product of Example 5b, in 30 ml of DMSO. After stirring for 3 hours, the reaction mixture was poured into an icewater mixture (200 g). The aqueous solution was acidified and extracted twice with ethyl ether. The ether solution was washed with 2.8N NH$_4$OH solution in portions until the obtained aqueous solution was basic. The washed aqueous solutions were combined and acidified with 6N HCl. The acidified aqueous solution was extracted with ethyl ether, the organic layer was washed with H$_2$O and dried over MgSO$_4$. Removal of the solvent yielded a yellow residue which was treated with excess CH$_2$N$_2$-ether solution to obtain the methyl ester. The methyl ester was purified by preparative HPLC using petroleum ether EtOAc (20:1) as the eluent and subsequent distillation through a Kugelrohr apparatus, bp 125°-140° C./0.02 mmHg.

A mixture of 5.6 g of the thus obtained methyl ester, 6.5 g of potassium carbonate, 40 ml of methanol, and 15 ml of H$_2$O was stirred for 3 days. The aqueous solution was acidified and extracted with ethyl ether. The organic solution was dried over MgSO$_4$. The residue, after removal of solvent, was distilled through a Kugelrohr apparatus to give the title acid compound, bp 150°-160°/0.02 mm Hg.

Elemental Analysis:
Calculated for C$_{18}$H$_{26}$O$_4$: C, 70.56; H, 8.55.
Found (acid): C, 70.07; H, 8.43.

EXAMPLE 6
Methyl 7,7-dimethyl-8-(4-hydroxyphenylmethoxy)-5(Z)-octenoate

Formula (I): R$^1$=CH$_3$; R$^2$=CH$_3$; R$^3$=4-OH; X=—CH$_2$OCH$_2$—; Y=—CO$_2$CH$_3$.

In a flask was placed 3.75 g (0.156 mole) of NaH and 50 ml of DMF under an atmosphere of N$_2$. A solution of 10.8 ml of ethanethiol in 20 ml DMF was added with stirring at room temperature. While stirring for 30 minutes, a solution of 6.3 g of methyl 7,7-dimethyl-8-(4-methoxyphenylmethoxy)-5(Z)octenoate, the methyl ester prepared in Example 5c, in 20 ml of DMF was added. The resulting mixture was heated to 90°-95° C. for one day. The reaction mixture was poured into an ice-water mixture, acidified with 6N HCl and then extracted with ethyl ether. The organic solution was washed with H$_2$O, NaCl solution, and dried over Na$_2$SO$_4$. Solvent was removed on a rotary evaporator and the residue was dissolved in ethyl ether followed by addition of a solution of excess CH$_2$N$_2$ in ether. The crude product was purified by a silica gel column using EtOAc-petroleum ether (1:6) as an eluant to obtain the title compound, an oil.

Elemental Analysis:
Calculated for C$_{18}$H$_{26}$O$_4$: C, 70.56; H, 8.55.
Found: C, 69.80; H, 8.48.

EXAMPLE 7
7,7-Dimethyl-8-(4-hydroxyphenylmethoxy)-5(Z) Octenoic Acid

Formula (I): R$^1$=CH$_3$; R$^2$=CH$_3$; R$^3$=4—OH; X=—CH$_2$OCH$_2$—; Y=—CO$_2$H.

A mixture of 1.98 g of methyl 7,7-dimethyl-8-(4-hydroxyphenylmethoxy)-5(Z)octenoate, the product of Example 6, 4 g of potassium carbonate, 30 ml of methanol and 20 ml water was stirred at room temperature for two days. The aqueous solution was acidified with 6N HCl and extracted with ethyl ether. The organic solution was washed with H$_2$O, and dried over MgSO$_4$. The residue, after removal of solvent, was purified by a silica gel column using CH$_2$Cl$_2$- MeOH (10:1) as an eluant to obtain the title compound, an oil.

Elemental Analysis:
Calculated for C$_{17}$H$_{24}$O$_4$: C, 69.84; H, 8.27.
Found: C, 69.37; H, 8.30.

EXAMPLE 8 a. Methyl 7,7-dimethyl-8-hydroxy-5(Z)octenoate

In a dry flask equipped with a mechanical stirrer, a dry-ice condenser, and a gas bubbler was introduced 100 ml of liquid NH$_3$ and then 8.67 g of 7,7-dimethyl-8-(phenylmethoxy)-5(Z)Octenoic acid, the product of Example 1c. Sodium metal in small portions was added until the blue color of the reaction mixture was persistent. The reaction was then quenched by addition of NH$_4$Cl. NH$_3$ was removed by bubbling N$_2$ gas. The residue was dissolved in H$_2$O and acidified with 6N HCl. The aqueous solution was extracted with ethyl ether. The organic solution was washed with H$_2$O, NaCl solution and dried over MgSO$_4$. To the solution was added excess CH$_2$N$_2$ in ethyl ether solution and the solvent was removed to give a residue. The residue was distilled to yield the title compound, bp 90°/0.05 mm Hg.

b. Methyl 7,7-dimethyl-8-oxo-5(Z)octenoate

In a three-neck flask equipped with a mechanical stirrer and an addition funnel was placed 24 g (0.069 mole) of pyridinium dichromate and 120 ml of CH$_2$Cl$_2$. The mixture was stirred vigorously then a solution of 6.73 g of methyl 7,7-dimethyl-8-hydroxy-5(Z)octenoate, the product of Example 8a, in 20 ml of CH$_2$Cl$_2$ was added in one portion. The reaction mixture was stirred continuously for 24 hours, and then poured into 200 ml of ethyl ether. The resulting mixture was filtered through a column packed with silica gel to obtain a colorless filtrate. The residue after removal of solvent was distilled to give the title compound, bp 75°-82°/0.02 mm Hg.

c. Methyl 9-(4-chlorophenyl)-7,7-dimethyl-5(Z),8-nonadienoate

Formula (I): R$^1$=CH$_3$; R$^2$=CH$_3$; R$^3$=4—Cl; X=—CH=CH—; Y=—CO$_2$CH$_3$.

In a dry three-neck flask equipped with an addition funnel and a mechanical stirrer under an atmosphere of N$_2$ was placed 120 ml of THF and 9.5 g (0.0224 mole) of 4-chlorobenzyltriphenylphosphonium chloride (Alfa) and 4.1 g (0.0224 mole) of N-sodiumhexamethyldisilazane (from Petrarch Systems Inc.). The mixture as allowed to stir at room temperature for 0.5 hours, then a solution of 3.8 g (0.019 mole) of methyl 7,7-dimethyl-8 oxo-5(Z)octenoate, the product of Example 8b, in 20 ml of THF was added dropwise. The reaction mixture was stirred at room temperature for 12 hours and then at 70° C. for 4 hours. The resulting mixture was allowed to cool to room temperature and then was poured into an ice-water mixture. The aqueous solution was acidified with 1N HCl and extracted with ether three times. The organic solution was washed with H$_2$O, 5% NaHCO$_3$ solution, NaCl solution and dried over Na$_2$SO$_4$. The residue, after removal of solvent, was purified through a silica gel column using hexane-ethyl acetate as an eluant to give the title compound, an oil.

Elemental Analysis:

Calculated for C$_{18}$H$_{23}$ClO$_2$: C, 70.46; H, 7.56; Cl, 11.55.

Found: C, 70.51; H, 7.58; Cl, 11.61.

Example 9

9-(4-Chlorophenyl)-7,7-dimethyl-5(Z),8-nonadienoic acid

Formula (I): R$^1$=CH$_3$; R$^2$=CH$_3$; R$^3$=4—Cl; X=—CH=CH—; Y=COOH.

A mixture of 2.83 g of methyl 9-(4-chlorophenyl)-7,7-dimethyl 5(Z),8-nonadienoate, the product of Example 8c, 5.2 g of potassium carbonate, 60 ml of methanol, and 15 ml of water was stirred at room temperature for 24 hours. Methanol was removed and the residue was diluted with 50 ml of H$_2$O and extracted with ether one time to remove the unreacted starting material. The aqueous solution was acidified with 6N HCl and then extracted with ethyl ether two times. The organic layer was washed with NaCl solution, dried over MgSO$_4$. Removal of solvent obtained the title compound, an oil.

Elemental Analysis:

Calculated for C$_{17}$H$_{21}$ClO$_2$: C, 69.73; H, 7.23; Cl, 12.11.

Found: C, 69.61; H, 7.26; Cl, 12.12.

EXAMPLE 10 a. 2,2-Dimethyl-3-(3-phenyl-2-propenoxy)propanol

In a dry three-neck flask under an atmosphere of N$_2$ was placed 14.4 g (0.6 mole) of NaH and 100 ml of DMF. The mixture was stirred and a solution of 52.1 g (0.5 mole) of 2,2-dimethylpropandiol in 75 ml of DMF was added dropwise. Stirring was continued until the gas evolution ceased, then a solution of 91.57 g (0.6 mole) of 3-phenyl-2-propenyl chloride in 50 ml of DMF was added. The reaction mixture was stirred at room temperature for two days, then poured into 500 ml of ice and water. The aqueous solution was extracted with three 300 ml portions of ethyl ether. The organic layers were combined and washed with H$_2$O, saturated NaCl solution, and then dried over MgSO$_4$. The solvent was removed on a rotary evaporator to give a brick red liquid. Kugelrohr distillation gave the title compound, bp 100°-110°/0.025-0.005 mm Hg. The product was a mixture of cis and trans isomers.

b. 2,2-Dimethyl-3-(3-phenyl-2-propenoxy)propionaldehyde

In a dry three-neck flask equipped with a mechanical stirrer and an addition funnel was placed 128 g of pyridinium dichromate and 320 ml of dry CH$_2$Cl$_2$. The mixture was vigorously stirred and a solution of 32.37 g (0.147 mole) of 2,2-dimethyl-3-(3-phenyl-2-propenoxy)-propanol, the product of Example 10a, in 50 ml of CH$_2$Cl$_2$ was added in one portion. The reaction mixture was stirred at room temperature for three days and then was poured into 400 ml of ethyl ether. The resulting mixture was filtered through a column packed with dry silica gel to obtain a yellow filtrate. The filtrate was concentrated to obtain a yellow residue. Kugelrohr distillation of the residue gave the title compound, bp 90°/0.05 mm Hg.

c. 7,7-Dimethyl-8-(3-phenyl-2-propenoxy)-5(Z)octenoic Acid

Formula (I): R$^1$=CH$_3$; R$^2$=CH$_3$; R$^3$=H; X=—CH=CH—CH$_2$OCH$_2$—; Y=—COOH.

In a dry three-neck flask under an atmosphere of N$_2$ equipped with a mechanical stirrer, an addition funnel and a gas bubbler was placed 5.28 g (0.22 mole) of NaH and 110 ml of dry DMSO. The mixture was heated to 80° C. for about 45 minutes. The resulting green solution was cooled with an ice-water bath and a solution of (4-carboxybuty)triphenylphosphonium bromide in 125 ml of DMSO was added. The obtained reddish mixture was stirred at room temperature for 1 hour. Then a solution of 20 g (0.092 mole) of 2,2-dimethyl-3-(3-phenyl-2-propenoxy)propionaldehyde, the product of Example 10b, in 50 ml of DMSO was added. The resulting reaction solution was stirred at room temperature for two days and then was poured into 100 ml of H$_2$O. The aqueous solution was acidified with 6N HCl and extracted with ethyl ether three times. The organic layers were combined, washed with H$_2$O and then extracted with 10% NH$_4$OH solution. The NH$_4$OH extract was acidified with 3N HCl and extracted with Et$_2$O-hexane (1:1). The obtained organic solution was washed with H$_2$O, and dried over MgSO$_4$. Solvent was removed to give a clear golden oil. The title product was purified through the following successive procedures: Kugelrohr distillation, conversion to the corresponding methyl ester by treatment with $CH_2N_2$, silica gel column chromatography EtOAc-pet ether (1:30), saponification by $K_2CO_3$/MeOH/$H_2O$, and silica gel column chromatography $CHCl_3$—MeOH (100:1).

Elemental Analysis:
Calculated for $C_{19}H_{26}O_3$: C, 75.46; H, 8.69.
Found: C, 74.98; H, 8.41.

EXAMPLE 11 a. β, β-Dimethyl-1,3-dioxalane-2-ethanol

A mixture of 36 g of 2,2-dimethyl-3-hydroxypropionaldehyde [(prepared by the procedure described by E. T. Stiler, S. A. Harris, J. C. Keresztesy and K. Folker in J. Am. Chem. Soc. 1785 (1940)], 55 ml of ethylene glycol, 200 mg of p-toluenesulfonic acid monohydrate, and 300 ml of toluene was heated to reflux for 24 hours with a Dean Stark apparatus to remove water. The reaction mixture was washed with $NaHCO_3$ solution and dried over $Na_2SO_4$. The title compound was obtained by distillation, bp 50°–54°/0.4–0.3 mm Hg.

b. Methyl 2-(1-pentenyl)benzenecarboxylate

In a dry three-neck flask equipped with a mechanical stirrer, an addition funnel, and a gas bubbler under an atmosphere of $N_2$ was placed 175 ml of dry DMSO and 3.78 g (0.16 mole) of NaH. The mixture was heated to 80° C. for 45 minutes and then cooled to room temperature. A mixture of 60 g (0.15 mole) of butyltriphenylphonium bromide (Aldrich) in 30 ml of DMSO was added. After stirring for 1 hour a solution of 24.6 g (0.15 mole) of 2-methylcarboxybenzaldehyde [prepared via the procedure described by C. Brown and M. V. Sargent in J. Chem. Soc. (C) 1818 (1969)] in 30 ml DMSO was added. The reaction mixture was stirred at 30°–40° C. for 4 hours and then was poured into an ice-water mixture. The aqueous solution was extracted with ethyl ether three times. The organic layers were combined and washed with $H_2O$, saturated NaCl solution, and dried over $MgSO_4$. The solvent was removed to give a residue. Distillation gave the title compound, as a cis and trans mixture bp 85°–90°/0.025 mm Hg.

c. 2-(1-Pentenyl)benzenemethanol

A solution of 9.70 g of methyl 2-(1-pentenyl)benzenecarboxylate, the product of Example 11b, was added to a mixture of 1.69 g lithium aluminum hydride and 300 ml of ethyl ether with stirring. After stirring for 0.5 hour, the reaction was quenched by successive additions of 1.7 ml of $H_2O$, 1.7 ml of 15% NaOH, and 5.1 ml of $H_2O$. The white solid was filtered and the filtrate was concentrated to obtain a yellow oil. Distillation gave the title compound, as a mixture of cis and trans isomers, bp 91°–102°/0.025 mm Hg.

d. 1-Bromomethyl-2-(1-pentenyl)benzene

The mixture of 8.63 g 2-(1-pentenyl)benezenemethanol, the product of Example 11c, 100 ml of ethyl ether, and 5.0 ml of phosphorous tribromide was heated to reflux for 2 hours. The reaction mixture was poured into a mixture of ice and water and the aqueous solution was extracted with ether. The ether was removed to give the title compound.

e. 2-[1,1-Dimethyl-2-[[2-(1-pentenyl)phenyl]methoxy]ethyl1,3-dioxolane

In a dry three-neck flask under an atmosphere of $N_2$ was placed 1.06 g (0.044 mole) of NaH and 30 ml of DMF. A solution of 6.50 g (0.045 mole) of β,β-dimethyl-1,3-dioxolane-2-ethanol, the product of Example 11a, in 20 ml of DMF was added dropwise. The resulting solution was stirred at room temperature for 1 hour then a solution of 10.6 g (0.044 mole) of 1-bromomethyl-2-(1-pentenyl)benzene, the product of Example 11d, in 20 ml DMF was added. After stirring for 12 hours, the reaction mixture was poured into an ice-water mixture and the aqueous was extracted with ether. The organic layer was washed with saturated NaCl solution and dried over $MgSO_4$. The solvent was removed to give a yellow residue. Silica gel column chromatography using EtOAc-pet. ether (1:30) as an eluant afforded the pure title compound.

Elemental Analysis:
Calculated for $C_{19}H_{28}O_3$: C, 74.96; H, 9.27
Found: C, 74.18; H, 9.18 f. 2,2-Dimethyl-3-[2-(1-pentenyl)phenyl)methoxy]propionaldehyde

A mixture of 7.3 g of [2-[1,1-dimethyl-2-[[2-(1-pentenyl)phenyl]methoxy]ethyl-1,3-dioxolane, the product of Example 11e, 20 ml of 6N HCl, 40 ml of $H_2O$, and 150 ml of THF was heated to 60° C. for 16 hours. THF was removed on a rotary evaporator and the aqueous solution was extracted with ethylether. The organic solution was washed with 10% $NaHCO_3$ solution, and saturated NaCl solution and dried over $MgSO_4$. The solvent was removed to give the title compound as a cis and trans mixture.

g. 7,7-Dimethyl-8-[2(1-pentenyl)phenylmethoxy]-5(Z)octenoic acid

Formula (I): $R^1 = CH_3$; $R^2 = CH_3$; $R^3 = -CH=CH(CH_2)_2CH_3$; $X = -CH_2OCH_2-$; $Y = -COOH$.

In a dry three-neck flask equipped with a mechanical stirrer and an addition funnel was placed 5.76 g (0.24 mole) of NaH and 280 ml of DMSO. The mixture was heated to 85° C. for 1 hour and then was cooled to room temperature. A sample of (4-carboxybutyl)triphenylphosphonium bromide (53.2 g; 0.12 mole) was added. The resulting reddish reaction mixture was stirred for an additional one hour at room temperature and then was cooled with an ice-water bath. A solution of 28 g of 2,2-dimethyl-3-[2-(1-pentenyl)phenylmethoxy]propionaldehyde, the product of Example 11f, in 60 ml of DMSO was added. The reaction mixture was stirred at room temperature overnight and then was poured into 300 ml of ice water mixture. The aqueous solution was acidified with 6N HCl and extracted with ethyl ether. The ether solution was washed with 10% $NH_4OH$ solution. The aqueous $NH_4OH$ solution was acidified with 6N HCl solution and then was extracted with ethyl ether. The ether solution was washed with NaCl solution and dried over $Na_2SO_4$. The solvent was removed on a rotary evaporator to give a residue. Silica gel column chromatogrphy $CHCl_3$-MeOH (100:3) of the residue gave the title compound. The title compound was distilled through a Kugelrohr apparatus, bp 165°–175°/0.04 mm Hg.

Elemental Analysis:
Calculated for $C_{22}H_{32}O_3$: C, 76.70; H, 9.36.
Found : C, 76.68; H, 9.38.

What is claimed is:

1. An aryl fatty acid compound of the following formula (I):

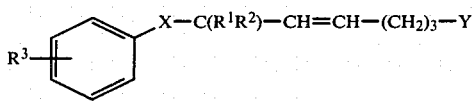

wherein
- $R^1$ and $R^2$ are independently hydrogen, methyl or fluorine or taken together are ethylene of the formula —$CH_2CH_2$—;
- $R^3$ is hydrogen, alkyl, alkoxy, alkylthio, halo, alkenyl or hydroxy;
- X is —$CH_2OCH_2$—, —CH=CH—, or —CH=CH—$CH_2$—O—$CH_2$—;
- Y is COOH, alkoxycarbonyl, —$CONH_2$, —$CONHR^4$, —$CONR^5R^6$, or hydroxyalkyl;
- $R^4$ is alkyl or hydroxy;
- $R^5$ is alkyl;
- $R^6$ is alkyl; and, when Y is —$CO_2H$, the pharmaceutically acceptable base addition salts thereof.

2. The aryl fatty acid compound of claim 1, wherein
- $R^1$ and $R^2$ are independently hydrogen, methyl or fluorine or taken together are ethylene of the formula —$CH_2CH_2$—;
- $R^3$ is hydrogen, lower alkyl of about 1 to 6 carbons, loweralkoxy of about 1 to 4 carbons, loweralkylthio of about 1 to 4 carbons, fluoro, chloro, bromo, iodo, alkenyl of about 2–6 carbons, or hydroxy;
- X is —$CH_2OCH_2$—, —CH=CH—, or —CH=CH—$CH_2OCH_2$—;
- Y is COOH, loweralkoxycarbonyl wherein the lower alkoxy moiety is about 1 to 4 carbons, —$CONH_2$, —$CONHR^4$, $CONR^5R^6$, or —$CH_2OH$;
- $R^4$ is loweralkyl of about 1 to 4 carbons or hydroxy; and $R^5$ and $R^6$ are the same or different and are lower alkyl of about 1–4 carbons.

3. The aryl fatty acid compound of claim 1 wherein $R^1$ is methyl.

4. The aryl fatty acid compound of claim 1 wherein $R^1$ and $R^2$ are both methyl.

5. The aryl fatty acid compound of claim 1 wherein $R^3$ is hydrogen.

6. The aryl fatty acid compound of claim 1 wherein Y is —COOH.

7. The aryl fatty acid compound of claim 1 wherein X is —$CH_2OCH_2$—.

8. The aryl fatty acid compound of claim 1 wherein the 5-position double bond is in the cis-configuration.

9. The aryl fatty acid compound of claim 1 wherein said aryl fatty acid is selected from the group consisting of
- 7,7-dimethyl-8-(phenylmethoxy)-5(Z)-octenoic acid;
- N,N,7,7-tetramethyl-8-(phenylmethoxy)-5(Z)-octenamide;
- ethyl 7,7-dimethyl-8-(phenylmethoxy)-5(Z)-octenoate;
- 7,7-dimethyl-8-(phenylmethoxy)-5(Z)-octen-1-ol;
- 7,7-dimethyl-8-(4-methoxyphenyl)methoxy-5(Z)-octenoic acid;
- methyl 7,7-dimethyl-8-(4-methoxyphenyl)methoxy-5(Z)octenoate;
- methyl 8-(4-hydroxyphenylmethoxy)-7,7-dimethyl-5(Z)octenoate;
- 8-(4-hydroxyphenylmethoxy)-7,7-dimethyl-5(Z)octenoic acid;
- methyl 7,7-dimethyl-8-(phenylmethoxy)-5(Z)octenoate;
- methyl 9-(4-chlorophenyl)-7,7-dimethyl-5(Z), 8-nonadienoate;
- 9-(4-chlorophenyl)-7,7-dimethyl-5(Z), 8-nonadienoic acid;
- 7,7-dimethyl-8-(3-phenyl-2-propenoxy)-5(Z)-octenoic acid; and
- 7,7-dimethyl-8-[[2-(1-pentenyl)phenyl]methoxy]-5(Z)octenoic acid.

10. The aryl fatty acid compound of claim 1 wherein said fatty acid is 7,7-dimethyl-8-(phenylmethoxy)-5(Z)-octenoic acid.

11. A pharmaceutical composition which comprises an aryl fatty acid of claim 1 in association with a pharmaceutically acceptable diluent or carrier.

* * * * *